Figure 1:
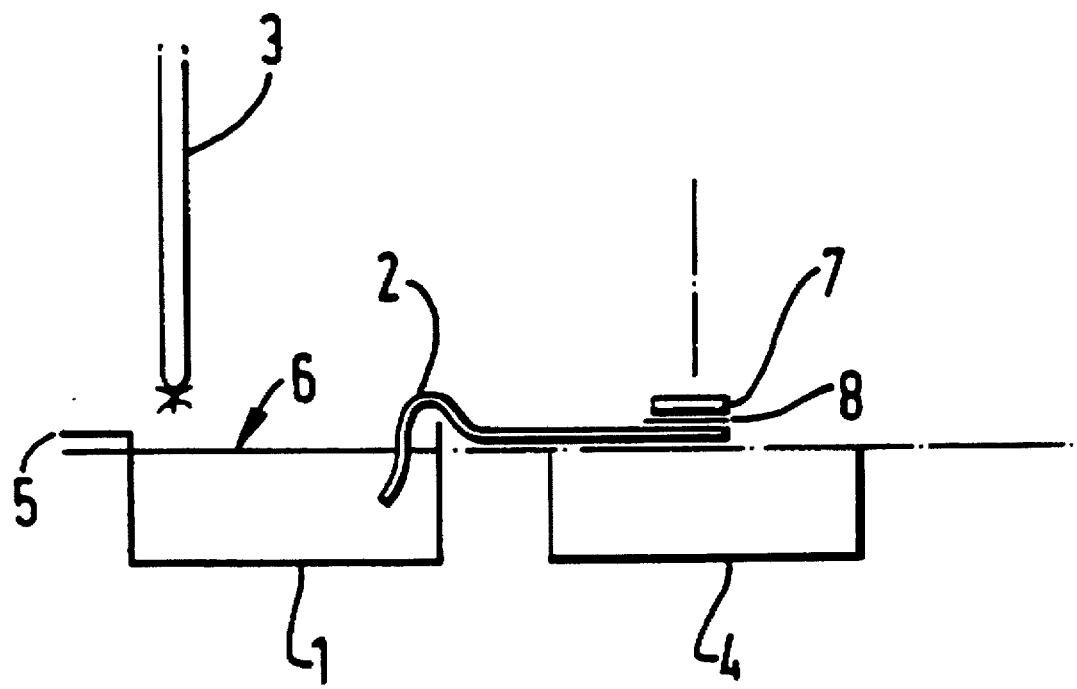

United States Patent [19]

Fenton et al.

[11] Patent Number: 5,714,232
[45] Date of Patent: Feb. 3, 1998

[54] ALGINATE FABRIC, ITS USE IN WOUND DRESSINGS AND SURGICAL HAEMOSTATS AND A PROCESS FOR ITS MANUFACTURE

[75] Inventors: John Charles Fenton, Bargoed, United Kingdom; Allison Frances Keys, St. Louis, Mo.; Peter Michael John Mahoney, Llangollen, United Kingdom

[73] Assignee: E. R. Squibb & Sons, Inc., Princeton, N.J.

[21] Appl. No.: 547,385

[22] Filed: Oct. 24, 1995

Related U.S. Application Data

[63] Continuation of Ser. No. 137,151, Oct. 21, 1993, abandoned.

[30] Foreign Application Priority Data

May 1, 1991 [GB] United Kingdom .................. 9109367

[51] Int. Cl.$^6$ .................. D04H 1/54; A61L 15/00
[52] U.S. Cl. .................. 428/171; 428/76; 428/102; 442/402; 442/414; 602/42; 602/45; 602/49; 264/175; 264/293; 264/257; 264/284; 264/319
[58] Field of Search .................. 428/76, 170, 171, 428/102; 602/42, 45, 49; 264/175, 293, 257, 284, 319; 442/402, 414

[56] References Cited

U.S. PATENT DOCUMENTS

| | | | |
|---|---|---|---|
| 4,035,483 | 7/1977 | Bunyan | 424/665 |
| 4,088,726 | 5/1978 | Cumbers | 264/123 |
| 4,100,324 | 7/1978 | Anderson et al. | 428/288 |
| 4,128,612 | 12/1978 | Roth | 264/126 |
| 4,170,680 | 10/1979 | Cumbers | 428/195 |
| 5,197,945 | 3/1993 | Cole et al. | 602/49 |
| 5,242,435 | 9/1993 | Murji et al. | 604/274 |

FOREIGN PATENT DOCUMENTS

| | | |
|---|---|---|
| 0 072 680 | 8/1982 | European Pat. Off. . |
| 0 160 560 | 4/1985 | European Pat. Off. . |
| 0 344 913 | 4/1989 | European Pat. Off. . |
| 1 379 158 | 2/1973 | United Kingdom . |
| WO 80/02300 | 10/1980 | WIPO . |
| WO 89/12471 | 12/1989 | WIPO . |

*Primary Examiner*—Kathleen Choi
*Attorney, Agent, or Firm*—Theodore R. Furman, Jr.; John M. Kilcoyne

[57] ABSTRACT

The invention is a wound dressing prepared from alginate fibers which have good structural integrity, whereby layers are firmly joined together, e.g. by stitching or calendering at a plurality of points to produce a composite fabric.

19 Claims, 1 Drawing Sheet

5,714,232

ALGINATE FABRIC, ITS USE IN WOUND DRESSINGS AND SURGICAL HAEMOSTATS AND A PROCESS FOR ITS MANUFACTURE

This is a continuation of application Ser. No. 08/137,151, filed Oct. 21, 1993, now abandoned.

The present invention relates to an alginate fabric. More particularly, the invention concerns a wound dressing or surgical haemostat formed from a nonwoven fabric of alginate fibres which has high absorbency and good integrity and to a process for the preparation of such a fabric.

Alginate fibres have been known for some time as being useful in the preparation of surgical dressings. For example, United Kingdom Patent No. 653341, published in 1951, describes surgical dressings formed from fibres of calcium alginate.

Various types of dressing formed from fabrics comprising alginate fibres are known. For example, a surgical dressing comprising a carded web of layered alginate fibres is known; and Kaltostat haemostatic wound dressing is a carded and needle-tacked web of alginate fibres.

During surgery, it is necessary to remove blood from the wound in order to afford the surgeon a clear view. For use in surgery, where a wound is bleeding freely, the ideal dressing will be haemostatic and will have good structural integrity, high absorbency and a high liquid retention capacity. Good integrity is particularly important for a dressing for use in surgery since it must be possible to lift the whole dressing away from the wound when saturated in blood. High absorbency means that an efficient uptake of exudate or blood, together with its associated toxins and other undesirable matter, can be achieved. A high liquid retention capacity means that blood is retained within the dressing when it is removed from the wound and dripping of blood is minimised.

Conventionally this is achieved by providing absorbent material in the form of cotton or cotton and viscose gauze. While such materials have good absorbency, they have low liquid-retention capabilities. There is therefore a risk when such dressings are used that surrounding areas will be contaminated with blood, and this risk has assumed particular importance in view of current concern regarding infectious diseases such as Aids and hepatitis B.

Furthermore, the gauze dressings currently used in surgery are not haemostatic, that is to say, they do not inhibit bleeding.

Presently available haemostatic alginate dressings are not suitable for use in surgery because they have insufficient structural integrity such that they tend to disintegrate.

EP-A-0344913 describes an alginate wound dressing of an integrity alleged to be such as to enable it to be lifted in one piece from a wound even when saturated with blood or other saline fluids. Briefly, the wound dressing provided by EP-A-0344913 comprises a non-woven fabric of alginate staple fibres, the fabric being substantially free from any adhesive binder or of interfusing of fibres at their crossing points. The required integrity is imparted to the dressing fabric of EP-A-0344913 by subjecting the non-woven web of staple alginate fibres to a hydraulic entanglement procedure which preferably comprises hydroentanglement.

Whilst the wound dressing provided by EP-A-0344913 is of good integrity, it does not have sufficiently high absorbency and liquid-retension capacity to be useful during surgery.

U.S. Pat. No. 3,937,223 discloses a haemostatic surgical felt comprising fibres of a polymer having glycolic acid ester linkages and which is completely absorbed when enclosed in living tissue. The felt has partially compressed heat embossed surfaces. This embossing is said to cause a reduction in the rate of penetration of blood. U.S. Pat. No. 3,937,223 contains no suggestion that its teaching could be extended to dressings prepared from different types of fibres. In particular, there is no suggestion that alginates could be used.

U.S. Pat. No. 4,128,612 (divided from above-mentioned U.S. Pat. No. 3,937,223) relates to a process for the manufacture of a haemostatic surgical felt having a textured and embossed surface. Briefly, the process includes the steps of randomly air laying fibres of a living tissue absorbable polymer into a mat and heating and compressing the mat so as to emboss it. U.S. Pat. No. 4,128,612 stresses the random formation of the mat and suggests that orientation of the fibres is to be avoided. There is no indication that the process described in the U.S. Pat. No. 4,128,612 could be applied to alginate fibres or that a layered mat of fibres could be used.

We have now found that dressings can be prepared from alginate fibres which fulfill the abovementioned criteria for a surgical haemostat.

The requisite good structural integrity can be imparted to the alginate dressing by firmly joining together layers of alginate material at a plurality of points to produce a composite fabric. This may be achieved, for example, by stitching, or, preferably, by calendering.

A BRIEF DESCRIPTION OF THE DRAWINGS

FIG. 1 depicts an apparatus for determining absorbency of absorbent materials.

We have surprisingly found that by embossing regions of the layered alginate fabric, for example, by stitching or calendering, a haemostatic material having good integrity is produced without substantially affecting the absorbency or liquid retention properties of the fabric.

The present invention accordingly provides a non-woven fabric suitable for use as a surgical haemostat comprising layers of alginate staple fibres, which layers are joined together at a plurality of points throughout the fabric whereby an embossed pattern is produced on at least one of the major external surfaces of the fabric. It is necessary that the embossed areas of the fabric should be of sufficient extent to impart integrity, but should not be so extensive that the absorbency of the finished fabric is adversely affected. Suitable ratios for embossed:unembossed area are in a range of 1:1 to 1:9. Preferably the ratio of embossed:unembossed area will be in the region of 1:4.

The present invention provides a non-woven fabric suitable for use as a surgical haemostat comprising layers of alginate staple fibres which layers are joined together at a plurality of points throughout the fabric whereby an embossed pattern is produced on at least one of the major external surfaces of the fabric wherein the ratio of embossed:unembossed area is in the range of 1:1 to 1:9.

The present invention further provides a non-woven fabric suitable for use as a surgical haemostat comprising layers of alginate staple fibres, which layers are joined together at a plurality of points throughout the fabric by stitching or calendering whereby an embossed pattern is produced on at least one of the major external surfaces of the fabric.

In a preferred aspect, the present invention provides a calendered, non-woven, fabric comprising layers of alginate staple fibres which fabric bears an embossed pattern on at least one of its major external surfaces.

Preferably both of the major external surfaces of the fabric according to the invention will bear an embossed pattern.

The haemostatic action of alginates is believed to be related to calcium ion release. On contact with blood or other saline fluids, calcium ions are released and exchanged for sodium ions. Calcium ions interact with the blood clotting cascade mechanism, resulting in clot formation.

We have now found that the degree of calcium ion release from alginate material can be controlled. This means that dressings can be produced to give the appropriate degree of calcium ion release for differing applications.

The degree of calcium ion release can be controlled by selecting an appropriate alginate source material and/or by treating the alginate so as to enhance its calcium ion release properties.

Suitable alginates for use in the invention include both water-soluble and water-insoluble alginates, but will preferably be water-insoluble alginates. A particular water-insoluble alginate for use in the invention is calcium alginate. Nevertheless, the calcium alginate may advantageously contain up to 1.5% by weight of sodium ions. Preferably 99% calcium alginate fibres will be used.

Alginic acid is a linear polymer comprising D-mannuronic acid and L-guluronic acid, the relative proportions of which vary with botanical source and state of maturation of the source plant. Alginates which comprise a high proportion of guluronic acid are known as high G alginates, and alginates which comprise a low proportion of guluronic acid are known as low G alginates.

Both high G alginates and low G alginates are suitable for use in the present invention.

High G alginates chelate calcium more strongly than do low G alginates. Thus, for applications where a high degree of calcium ion release is required, a low G alginate may be selected. For other applications, a high G alginate may be preferred. High G alginate may be obtained from, for example, *laminaria hyperborea*, and is commercially available as, for example, LF 10/60 from Protan Ltd. Low G alginate may be obtained from, for example, *ascophyllum nodosum*, and is commercially available as, for example, Lamitex (Protan Ltd.) and Manucol DM (Kelco).

We have now surprisingly found that calcium ion release from any particular alginate can be increased if the alginate material is treated with an oxidising agent. A particularly suitable oxidising agent for this purpose is hypochlorite ion.

According to a further or alternative aspect, the present invention provides a method of enhancing calcium ion release from alginate material which comprises treating the material with an oxidising agent.

For some surgical applications, it is desirable to provide means for detecting the presence of the dressing in the patient's body. Advantageously, X-ray detectable material may be incorporated into the dressing for this purpose.

We have further found that X-ray detectable material can be incorporated into the embossed fabric.

Thus the invention further provides a non-woven fabric suitable for use as a surgical haemostat comprising layers of alginate staple fibres, which layers are joined together at a plurality of points throughout the fabric whereby an embossed pattern is produced on at least one of the major external surfaces of the fabric, and containing X-ray detectable material.

X-Ray detectable material for use in the fabrics of the present invention may take the form of, for example, yarn, ribbon, tape or strip. It is important that the X-ray detectable material is soft and pliable. X-Ray opaque materials include, for example, barium sulphate, tungsten and bismuth. A number of carrier materials for the X-ray opaque material are commercially available, including PVC, polyurethane (PU) and silicon.

The preferred X-ray detectable material for use in the present invention is one or more PVC X-ray detectable strips containing barium sulphate.

Advantageously the X-ray detectable material may be at least partially bound to the alginate fabric. Where the carrier material comprises a thermally fusable material, such as a plastic, for example PVC or PU, bonding of the X-ray detectable material to the alginate fabric may be achieved by partially melting the carrier material before or during insertion of the X-ray detectable material into the fabric, or, preferably, during the embossing process.

Calendering is a process whereby a web of material is compressed, usually between heated rollers.

In order to produce an embossed pattern, at least one the rollers of the calender must have a textured surface. For example, one or both rollers may have a plurality of either engravings or, preferably, raised portions. Conveniently, only one of the rollers has a textured surface.

The effect of calendering with a textured roller is that areas of the fabric surface are compressed to different extents such that areas which are compressed to a lesser extent become raised relative to areas which undergo greater compression, resulting in an embossed pattern.

Even if only one of the rollers of the calender has a textured surface, an embossed pattern may be produced on both major external surfaces of the finished fabric. This is because the pressure of the textured roller on the surface of the fabric it contacts tends to cause a reverse or "negative" of the embossed pattern produced on that surface to be produced on the opposite major external surface of the fabric. This "negative" pattern is considerably less pronounced than the pattern produced by direct embossment.

Where a fabric having an embossed pattern on both of its major external surfaces is referred to herein it is to be understood that a fabric having one directly embossed surface and one surface bearing a "negative" of the embossed pattern is included.

The quality of the embossed pattern is dependent on the temperature, pressure and speed of the rollers during the calendering process. If the pattern is not firmly embossed the calendered regions of the fabric tend to revert and in a relatively short time the embossed effect is lost. We have found that best results are achieved using a roller speed of 1 to 40 meters per minute, preferably 1 to 10 meters per minute, more preferably 3 meters per minute at a temperature of about 80° C. to about 210° C., preferably 130° C. and a pressure of 1 ton to 15 tons, preferably approximately 6 tons.

The wind up tension should be kept to a minimum. Over tensioning the web as it is wound up will tend to stretch the material as it leaves the calender nip. This results in reduced absorbency of the final product.

The present invention therefore provides a process for the preparation of an alginate fabric of good absorbency and high structural integrity which comprises calendering regions of a web of non-woven layered alginate fibres so as to produce an embossed pattern on at least one major external surface of the web. Preferably the calendering process will be conducted at a temperature of from 80° C. to 210° C. and a pressure of from 1 ton to 15 tons.

Preferably the web of non-woven layered alginate fibres is produced by cross-lapping. Cross-lapping is a process whereby a web is built up by the sequential laying of layers of fibres one on another until a web of the desired weight is achieved. Conveniently, fibres in alternate layers are orientated orthogonally to each other, but this is not essential. Preferably the layers of alginate fibres produced by cross-lapping are tacked together using a needle punching procedure According to a further or alternative aspect, the present invention provides a process for incorporation of one or more X-ray detectable strips into an alginate fabric which process comprises the steps of:

(a) providing a lightweight web of layered alginate fibres;

(b) positioning one or more X-ray detectable strips between the web and a further web of layered alginate fibres;

(c) needling the whole together; and (d) calendering areas of the fabric.

In order to avoid damage to the X-ray detectable strip during calendering, at least one of the top and bottom rollers of the calender is provided with one or more grooves. Each X-ray detectable strip in the fabric is aligned so as to coincide with a groove in the roller. Alignment can be achieved manually, or automatically or semi-automatically using, for example, an optical, infra red or electronic control system.

The fabric prepared by the process according to the invention typically has absorbency in the region of 10.5 times its own weight and a water-retention capacity in the region of 9.5 times its own weight. This compares with absorbency in the region of 6.5 times its own weight and a water-retention capacity in the region of 6.5 times its own weight for conventional surgical gauze.

While the fabric according to the present invention is particularly suitable for use as a surgical haemostat, it will be appreciated that it can also advantageously be employed as a wound dressing for non-surgical applications. The fabric according to the present invention is also particularly suitable for use in dentistry.

As will be appreciated, the alginate fabric according to the invention can suitably be manufactured in a range of basis weights, typically from about 120 g/m² to about 360 g/m², preferably from about 160 g/m² to about 240 g/m², more preferably, about 180 g/m². The basis weight of a given fabric will generally be dependent upon the use, for example as a wound dressing or surgical haemostat, to which the fabric is to be put. By way of example, a basis weight in the region of 120 g/m² is indicated for a moderately exuding wound whereas a basis weight in the region of 280 g/m² is indicated for a heavily exuding or freely bleeding wound.

In another aspect, the present invention provides a wound dressing or surgical haemostat comprising a non-woven fabric comprising layers of alginate staple fibres which layers are joined together at a plurality of points throughout the fabric whereby an embossed pattern is produced, optionally containing X-ray detectable material.

In a further aspect, the present invention provides a method of treating a mammalian subject undergoing surgery, which method comprises applying to the site of surgery a surgical haemostat according to the present invention.

In a still further aspect, the present invention provides a method of treating a mammalian subject having a wound, which method comprises applying to the wound a wound dressing according to the present invention.

As used herein the term "wound" includes cut, sore, ulcer, blister, burn, rash or any other lesion or area of troubled skin.

The wound dressings or surgical haemostats formed from the alginate fabric according to the present invention will advantageously be conventional dressings well known in the art- Examples of suitable dressings include bandages, adhesive strip dressings, island dressings, pads of various kinds, surgical sponges and packs, ward dressings, and such articles as tampons which may, for example, be impregnated with an antifungal agent such as miconazole for the treatment of candidal vaginitis (vaginal thrush). Such dressings may conveniently be prepared by standard methods known from the art.

The dressings in accordance with the present invention will conveniently be packaged in a hermetically-sealed envelope and sterilised, e.g. with ethylene oxide or by gamma-irradiation.

The following non-limiting Example is intended to illustrate the present invention.

EXAMPLE 1

Calcium alginate fibre was prepared as described in Preparation 1 of WO-A-89/12471, crimped, staple cut and converted to non-woven fabric by a conventional carding, cross-lapping and needle punching technique.

The calender is heated to 130° C. Web (basis weight 180 g/m²) is loaded to the feed roller. A core is loaded to the wind up and locked in position. The web is laid on the top surface of the fabric leader and the X-ray detectable strip aligned with the grooves in the calender. The material is passed through the calender nip and collected on the wind up roller.

Test Method

The apparatus used in the determination of absorbency is depicted in FIG. 1, and consists of water bath 1 containing a 0.9% (w/w) aqueous saline solution, absorbent strip 2, burette 3, top-pan balance 4 and overflow 5.

The thickness of the absorbent strip 2 is substantially equivalent to that of the dressing 7. The filter paper 8 has substantially the same planar dimensions as the dressing 7 but not necessarily the same thickness.

The apparatus is set up with the surface 6 of the saline solution level with the top surface of the top-pan balance 4. The flow of liquid from the burette 3 is then adjusted to approximately 1.5 ml per minute. The absorbent strip 2 is then saturated and placed between the bath 1 and the balance 4, as depicted in FIG. 1. The balance 4 is then tared. A weighed dressing 7 and filter paper 8 (cut to size) is positioned as depicted in FIG. 1.

After six minutes the weight shown on the balance 4 is recorded. The dressing 7 and filter paper 8 are then removed and any residual weight on the balance 4 noted.

Absorbency is determined on the basis of the following equation:

$$\frac{\text{wt. of liquid}}{\text{absorbed}} = \frac{\text{total wt.}}{\text{on balance}} - \frac{\text{dry wt.}}{\text{dressing}} + \frac{\text{wt. of satd.}}{\text{filter paper}} + \frac{\text{residual wt.}}{\text{on balance}}$$

Results

Using the test method described above, the absorbencies of the fabric according to the invention, and of commercially available surgical gauze (4 layers), were determined and compared. In the former case twelve samples, and in the latter case six samples, of the fabric were taken and an average value for the absorbency was calculated. The results obtained were as follows:

TABLE I

Alginate fabric of Example 1

| Wt. of dressing (g) | Wt. of saline absorbed (g) | Wt. of saline absorbed per gram of dressing (g) |
|---|---|---|
| 1.14 | 10.21 | 10.61 |
| 0.87 | 8.20 | 9.43 |
| 0.84 | 8.31 | 9.90 |
| 1.20 | 13.68 | 11.40 |
| 1.16 | 12.18 | 10.50 |
| 0.98 | 10.61 | 10.82 |
| 0.95 | 10.35 | 10.89 |
| 1.23 | 13.18 | 10.71 |
| 1.18 | 12.20 | 10.33 |
| 1.31 | 14.13 | 10.78 |
| 1.12 | 12.14 | 10.83 |
| 1.06 | 11.20 | 10.56 |

TABLE II

GAUZE

| Wt. of dressing (g) | Wt. of saline absorbed (g) | Wt. of saline absorbed per gram of dressing (g) |
|---|---|---|
| 1.04 | 6.85 | 6.58 |
| 1.05 | 6.24 | 5.94 |
| 0.89 | 6.01 | 6.75 |
| 0.92 | 6.37 | 6.92 |
| 0.94 | 5.55 | 5.90 |
| 0.94 | 6.06 | 6.45 |

From Table I above, it can be calculated that the average absorbency of the alginate fabric of Example I is 10.56 g of saline per gram of dressing; whereas, from Table II, the average absorbency of commercial surgical gauze (4 layers) can be calculated to be 6.42 g of saline per gram of dressing.

Retention Studies

Samples of fabric according to the invention, and of commercially available surgical gauze (4 layers), were cut to size (approximately 5×10 cm) and placed in a dish. Sufficient calf serum was added to just cover the dressings. After 6 minutes the dressings were carefully removed, held on an edge and allowed to drip. The weight of liquid retained and that lost were recorded. The results obtained were as follows:

TABLE III

Alginate fabric of Example 1

| Wt. of dressing (g) | Wt. of serum retained (g) | Wt. of serum lost (g) |
|---|---|---|
| 0.98 | 9.38 | 1.21 |
| 0.82 | 8.38 | 0.91 |
| 1.03 | 8.78 | 0.84 |
| 0.92 | 8.53 | 1.06 |
| 0.99 | 9.26 | 1.21 |
| 0.84 | 9.18 | 0.73 |
| 0.97 | 9.01 | 1.33 |
| 1.02 | 9.20 | 0.91 |
| 1.13 | 10.10 | 0.57 |
| 1.01 | 9.78 | 0.83 |

TABLE IV

GAUZE

| Wt. of dressing (g) | Wt. of serum retained (g) | Wt. of serum lost (g) |
|---|---|---|
| 0.64 | 4.06 | 2.58 |
| 0.82 | 5.40 | 3.12 |
| 0.84 | 5.26 | 3.46 |
| 0.93 | 6.21 | 3.81 |
| 1.12 | 7.13 | 4.71 |
| 0.76 | 4.73 | 3.05 |

From Table III above, it can be calculated that the average retention capacity of the alginate fabric of Example I is 9.48 g of serum per gram of dressing; whereas, from Table IV, the average retention capacity of commercial surgical gauze can be calculated to be 6.4 g of serum per gram of dressing.

We claim:

1. An article of manufacture comprising a non-woven fabric of alginate staple fibres wherein the alginate fibres are arranged in layers, which layers are joined together at a plurality of points throughout the fabric, whereby an embossed pattern is produced on at least one of the major external surfaces of the fabric wherein the ratio of embossed:unembossed area is in the range of 1:1 to 1:9.

2. An article as claimed in claim 1 wherein the ratio of embossed:unembossed area is about 1:4.

3. An article as claimed in claim 1 wherein the embossed pattern is produced by calendering.

4. An article as claimed in claim 1 wherein both major external surfaces bear an embossed pattern.

5. An article as claimed in claim 1 wherein the alginate staple fibres comprise 99% calcium alginate.

6. An article as claimed in claim 1 containing X-ray detectable material.

7. An article as claimed in claim 6 wherein the X-ray detectable material is one or more PVC strips containing barium sulphate.

8. An article as claimed in claim 6 wherein the X-ray detectable material is at least partially bound to the alginate fabric.

9. An article as claimed in claim 1 having a basis weight in the range of about 120 g/m$^2$ to about 360 g/m$^2$.

10. An article as claimed in claim 9 having a basis weight in the range of about 160 g/m$^2$ to about 240 g/m$^2$.

11. A process for the preparation of an article as claimed in claim 1 which comprises calendering regions of a web of non-woven, layered alginate fibres thereby producing an embossed pattern on at least one major external surface of the web.

12. A process as claimed in claim 11 wherein calendering is conducted at a temperature of from 80° C. to 210° C. and a pressure of from 1 ton to 15 tons.

13. A process as claimed in claim 11 further comprising incorporating one or more X-ray detectable strips into an alginate fabric comprising the steps of:
 (a) providing a lightweight web of layered alginate fibres;
 (b) positioning one or more X-ray detectable strips between the web and a further web of layered alginate fibres;
 (c) needling the whole together; and
 (d) calendering areas of the fabric.

14. An article as claimed in claim 1 being a surgical haemostat.

15. An article as claimed in claim 1 being a wound dressing.

16. A method of treating a mammalian subject having a wound which method comprises applying to the wound a wound dressing as claimed in claim 15.

17. A method of treating a mammalian subject undergoing surgery which comprises applying to the site of surgery a surgical haemostat as claimed in claim 14.

18. An article of manufacture having a basis weight of about 180 g/m$^2$ comprising a non-woven fabric of alginate staple fibres wherein the fabric comprises layers of 99% calcium alginate staple fibres, the layers are joined together at a plurality of points throughout the fabric by calendering such that an embossed pattern is produced on both major external surfaces of the fabric and the ratio of embossed:unembossed area is about 1:4, and which fabric contains at least one PVC strip containing barium sulphate wherein the PVC strip is, or the PVC strips are, partially bonded to the alginate fabric.

19. An article of manufacture having a basis weight of about 180 g/m$^2$ comprising a non-woven fabric of alginate staple fibres wherein the fabric comprises layers of 99% calcium alginate staple fibres, the layers are joined together at a plurality of points throughout the fabric by calendering such that an embossed pattern is produced on both major external surfaces of the fabric and the ratio of embossed:unembossed area is about 1:4, and which fabric contains at least one PVC strip containing barium sulphate.

* * * * *